(12) United States Patent
Park et al.

(10) Patent No.: US 12,637,402 B2
(45) Date of Patent: May 26, 2026

(54) CRESOL PREPARATION METHOD FOR INHIBITING PRODUCTION OF BYPRODUCT

(71) Applicant: Hanwha Solutions Corporation, Seoul (KR)

(72) Inventors: Jinho Park, Daejeon (KR); Kyuho Song, Daejeon (KR); Ji Hye Choi, Daejeon (KR); Namjin Jang, Daejeon (KR)

(73) Assignee: Hanwha Solutions Corporation, Seoul (KR)

( * ) Notice: Subject to any disclaimer, the term of this patent is extended or adjusted under 35 U.S.C. 154(b) by 506 days.

(21) Appl. No.: 18/259,083

(22) PCT Filed: Dec. 24, 2021

(86) PCT No.: PCT/KR2021/019829
§ 371 (c)(1),
(2) Date: Jun. 23, 2023

(87) PCT Pub. No.: WO2022/139546
PCT Pub. Date: Jun. 30, 2022

(65) Prior Publication Data
US 2024/0051906 A1 Feb. 15, 2024

(30) Foreign Application Priority Data
Dec. 24, 2020 (KR) ........................ 10-2020-0183739

(51) Int. Cl.
*C07C 37/02* (2006.01)
*C07C 37/72* (2006.01)

(52) U.S. Cl.
CPC .............. *C07C 37/02* (2013.01); *C07C 37/72* (2013.01)

(58) Field of Classification Search
CPC ................................ C07C 37/02; C07C 37/72
See application file for complete search history.

(56) References Cited

FOREIGN PATENT DOCUMENTS

| | | | |
|---|---|---|---|
| CN | 103254039 A | 8/2013 | |
| CN | 103992210 A | 8/2014 | |
| DE | 19633608 A1 * | 2/1998 | .............. C07C 37/02 |
| KR | 20170059824 A | 5/2017 | |
| KR | 20170106804 A | 9/2017 | |
| KR | 101819217 B1 | 1/2018 | |

* cited by examiner

*Primary Examiner* — Sikarl A Witherspoon
(74) *Attorney, Agent, or Firm* — Harvest IP Law, LLP

(57) ABSTRACT

The present invention relates to a cresol preparation method, wherein DTE, a byproduct produced by the cresol preparation method, is separated and recycled to a reaction step, thereby inhibiting the production of DTE.

The cresol preparation method according to the present invention is a process in which a cresol is prepared by a reaction of halo-toluene and a basic aqueous solution, and the method comprises a step of separating DTE, a byproduct of the process, and re-feeding DTE to the reaction step of halo-toluene and the basic aqueous solution.

8 Claims, No Drawings

CRESOL PREPARATION METHOD FOR INHIBITING PRODUCTION OF BYPRODUCT

CROSS-REFERENCE TO RELATED APPLICATION(S)

This application is a National Stage of International Application No. PCT/KR2021/019829 filed on Dec. 24, 2021, claiming priority based on Korean Patent Application No. 10-2020-0183739 filed on Dec. 24, 2020, the disclosure of which is incorporated herein by reference in its entirety.

TECHNICAL FIELD

The present invention relates to a method of preparing cresol, and more particularly, to a method of preparing cresol, which may suppress production of ditolyl ether (DTE) produced as a by-product in a binary system reaction to increase a cresol yield.

BACKGROUND ART

Cresol is used as a local anesthetic, a disinfectant, a fumigant, an industrial solvent, a herbicide, a surfactant, and the like, and, in particular, is also used a lot as a basic raw material for organic synthesis in various medical and chemical fields such as preparation of synthetic resins such as a semiconductor sealant, preparation of basic petrochemical products, pharmaceuticals, and the like.

Cresol is found in a tar acid form in various kinds of plants (wood tar), crude oil, coal tar, and the like, and is also produced by natural organic matter which is decomposed by microorganisms in soil and water.

A cresol-like compound may be obtained from those included in a naturally existing mixture by distilling or purifying, or obtained by organic synthesis.

However, since many materials having physical and chemical properties similar to cresol, such as pyridine, methyl pyridine, aniline, and xylenol, are included in the natural mixture such as coal tar and these materials remain in a purified resulting material also, it is not easy to obtain high-purity cresol and it is not appropriate for use for the above purpose, and thus, cresol is often prepared by organic synthesis.

Industrially, an alkylation reaction of phenol is often used, and a magnesium oxide-based catalyst or an iron-vanadium-based catalyst is often used, but the reaction has problems from the view point of harsh reaction conditions, catalytic activity, lifetime, and the like, and also has an environmental problem due to using heavy metals.

In particular, a magnesium oxide-based catalyst is used in a reaction process at a high temperature of about 350° C., and an iron-vanadium-based catalyst may be used at a lower temperature than the magnesium-based catalyst, but the catalyst may be easily inactivated.

In addition, in the alkylation reaction as above, xylenol, trimethylphenol, poly(alkyl)phenol polymer materials, and the like may be produced as a by-product to inhibit the reaction, and the by-products as such have a boiling point similar to cresol and are difficult to separate.

As a method for solving the problem, a method of preparing cresol by reacting halotoluene as a starting material with a basic aqueous solution is preferred due to its high yield, but since the method of preparing cresol produces a large amount of ditolyl ether (DTE) as a by-product, its separation cost is high.

DISCLOSURE

Technical Problem

An object of the present invention is to provide a novel method of suppressing the production of DTE which is produced by a side reaction when preparing cresol from halotoluene by a reaction with a basic aqueous solution in a reactor, thereby providing an effect of increasing a yield of cresol.

Technical Solution

In one general aspect, a method of preparing cresol by a process of reacting halotoluene and a basic aqueous solution includes: separating DTE which is a by-product of the process to refeed the DTE into the step of reacting the halotoluene and the basic aqueous solution.

In the method of preparing cresol according to an exemplary embodiment of the present invention, the method may include: reacting the halotoluene and the basic aqueous solution in a reactor; adding an acid for acidification; adding an organic solvent to extract cresol from an aqueous layer; and separating a by-product from the extracted cresol in the aqueous layer and refeeding the by-product into the reactor of the reaction step to perform the reaction.

In the method of preparing cresol according to an exemplary embodiment of the present invention, the acidification step may be a step of adding acid for acidification to a range of pH −5 to 2.5.

In the method of preparing cresol according to an exemplary embodiment of the present invention, the step of reacting halotoluene and a basic aqueous solution may be carried out under a condition of pH 11 or more.

In the method of preparing cresol according to an exemplary embodiment of the present invention, the step of reacting halotoluene and a basic aqueous solution may be carried out at a temperature of 100 to 450° C. under a pressure of 100 to 500 atm.

In the method of preparing cresol according to an exemplary embodiment of the present invention, the acidification step may be carried out using an acid having a pKa value of −2 or less.

In the method of preparing cresol according to an exemplary embodiment of the present invention, the organic solvent may be used at 10 to 200 parts by weight with respect to 100 parts by weight of the reaction product mixture including cresol.

In the method of preparing cresol according to an exemplary embodiment of the present invention, the step of extracting with an organic solvent may be repeated twice or more.

Advantageous Effects

According to the method of preparing cresol of the present invention, cresol may be prepared at a high yield and DTE which is produced by a side reaction is not produced anymore by chemical equilibrium, and thus, cresol may be obtained in a high yield.

BEST MODE

The present invention provides a method of preparing cresol by a process of reacting halotoluene and a basic aqueous solution, the method including: separating DTE produced by a side reaction of the process to refeed the DTE to a step of reacting the halotoluene and the basic aqueous solution to perform the reaction.

The DTE is produced as a side reacted product in producing cresol which is a reacted product of halotoluene and a basic aqueous solution, and it was found that DTE is produced in a certain amount of about 7 to 8 mol % by production of cresol in the reaction step and an equilibrium reaction and the production of DTE is suppressed using the equilibrium reaction to improve the yield of cresol.

The present inventors found that in order to suppress the equilibrium reaction, DTE produced in a reaction medium is artificially fed, thereby suppressing the production of DTE by an equilibrium reaction, thereby completing the present invention.

The DTE separated from the reaction step is recirculated and refed to the reaction step, thereby completing the present invention.

The reaction step of the present invention may use various types of reactors such as a batch reactor, a continuous reactor, or a plug flow reactor, and DTE which is a by-product from the reaction step may be separated from cresol by distillation or other methods in a later step and recirculated to a reactor in the reaction step.

Specifically, the preparation method of the present invention includes: reacting halotoluene and a basic aqueous solution; adding an acid for acidification; adding an organic solvent to extract cresol from an aqueous layer; and separating cresol and DTE from the extracted cresol and refeeding DTE into the reaction step.

According to an exemplary embodiment of the present invention, it is preferred that the step of reacting halotoluene and a basic aqueous solution is carried out under a condition of pH 11 or more.

Further, it is preferred that the reaction at this time is carried out at a temperature of about 200 to about 450° C. under a pressure of about 100 to about 500 atm.

According to an exemplary embodiment of the present invention, the acidification step may be carried out using an acid having a pKa value of −6 or less.

Further, it is preferred that in the acidification step, pH is adjusted to about 2.5 or less.

According to another exemplary embodiment of the present invention, it is preferred that the organic solvent has a DI value of 20 or less.

Further, it is preferred that the organic solvent is included at about 10 parts by weight to about 200 parts by weight with respect to 100 parts by weight of a reaction production mixture including cresol. Further, it is preferred that the step of extracting with the organic solvent is repeated twice or more.

In addition, in the present invention, separation of the cresol and DTE may be usually performed by distillation, but the separation means is not specified in the present invention.

Terms used in the present specification are used only for describing exemplary embodiments rather than limiting the present invention. Singular forms are intended to include plural forms unless otherwise indicated contextually. It should be understood that the terms "comprises", "provide", or "have" used in the present specification, are intended to specify the presence of practiced features, numerals, steps, constitutional elements, or a combination thereof, but do not preclude the presence or addition possibility of one or more other features, numerals, steps, constitutional elements, or a combination thereof.

Since the present invention may be variously modified and have various types, specific exemplary embodiments of the present invention will be illustrated and described in detail below. However, it is to be understood that the present invention is not limited to a specific disclosed form, but includes all of the modifications, equivalents, and substitutions within the spirit and technical scope of the present invention.

In the entire specification, the cresol covers all of ortho-, meta-, and para-cresol.

Further, halotoluene refers to a compound in which any one hydrogen of a benzene ring of toluene is substituted with a halogen atom including chlorine, bromine, and fluorine, and also covers all of ortho-, meta-, and para-forms.

Hereinafter, the present invention will be described in more detail.

First, a step of reacting halotoluene and a basic aqueous solution will be described.

It is preferred that in the reaction step of the present invention, the step of reacting halotoluene and a basic aqueous solution is carried out under a condition of pH 11 or more. It is preferred that a hydroxide ion to be used is derived from an aqueous solution of metal hydroxide such as sodium hydroxide, potassium hydroxide, calcium hydroxide, and barium hydroxide, but the present invention is not necessarily limited thereto.

That is, during a hydrolysis reaction for the reaction, a hydroxide ion may be added in excess compared with halotoluene, and after completing the reaction, an aqueous layer may show very strong basicity by the excessive hydroxide ions. Therefore, cresol which is the product is present as an anion in the aqueous layer, and due to the form, an equilibrium shift of the overall reaction may be toward a reacted product, thereby increasing a yield of cresol.

According to an exemplary embodiment of the reaction, it is preferred that the step of reacting halotoluene and a basic aqueous solution is carried out under a temperature condition of about 200 to about 450° C. and under a pressure condition of about 500 atm.

When a reaction temperature during the hydrolysis reaction is too low, a conversion rate of halotoluene and a selectivity and a yield of cresol may be decreased, and when the temperature is too high, an operation cost for operation at a high temperature becomes high, so that the economic feasibility for preparing cresol is poor.

In addition, when a reaction pressure is too low, the conversion rate of halotoluene and the selectivity and yield of cresol are decreased, and when the pressure is too high, the expenditure of a high pressure facility is increased.

During the hydrolysis reaction of the present invention, the product includes 7 to 8 mol % of ditolyl ether (DTE) produced by the chemical equilibrium reaction with cresol to produce a reacted product. The present inventors recognized that the DTE is inevitably produced by the equilibrium reaction, and when DTE produced in the reaction is refeed into the hydrolysis reaction step with raw materials, the feed amount is present in a reaction medium, so that equilibrium to produce DTE from cresol is induced to produce cresol, whereby DTE is not produced anymore to improve the yield of cresol and significantly decrease the amount of DTE produced which should be discarded as a by-product, and thus, an economical and environmentally friendly preparation method may be provided.

Meanwhile, most of the cresol isomers which are the product after the reaction are present in an aqueous layer in the form of cresol anions. Since it is impossible to commercialize cresol in the form of being dissolved in an aqueous layer, it is necessary to extract cresol from the aqueous layer.

Therefore, the present invention includes an acidification step of adding an acid after the substitution reaction.

According to an exemplary embodiment of the present invention, it is preferred to use a strong acid having a pKa value of about −6 or less in the acidification step. Specifically, for example, hydrochloric acid, chloric acid, chlorous acid, bromic acid, nitric acid, dilute sulfuric acid, and the like may be used, but the present invention is not necessarily limited thereto, and any strong acid which provides cresol anions or cresol with sufficient hydrogen atoms and may facilitate dissolution into an oil-soluble layer may be used without a particular limitation.

Further, according to another exemplary embodiment of the present invention, the acidification step may be adjusted to pH about 2.5 or less, preferably about −5 to about 2.5, and more preferably about −5 to about 1.5. When the pH is out of the range, a significant amount of the produced cresol compound remains in the aqueous layer to cause an environmental problem during reaction waste disposal.

As described above, cresol which is changed into an oil-soluble form by the acid treatment and DTE which is a by-product may be extracted from the aqueous layer by adding an organic solvent and obtained in the state of being dissolved in an organic solvent layer.

Herein, the usable organic solvent may be any organic solvent which may fractionate cresol in the aqueous layer, and it is preferred to use the organic solvent having a DI value of about 20 or less.

Specifically, for example, benzene, toluene, methyl-t-butyl ether (MTBE), methyl isobutyl ketone (MIBK), isobutyl acetate (iBA), or a mixture thereof may be used, and other than that, any organic solvent commonly used in the art to which the present invention pertains, such as hexane, heptane, cyclohexane, or xylene may be used without a particular limitation.

Further, according to another exemplary embodiment of the present invention, it is preferred to use the organic solvent at about 10 to about 200 parts by weight with respect to 100 parts by weight of a reaction production mixture including cresol.

When the organic solvent is used at less than 10 parts by weight with respect to the reaction product mixture including cresol, it is not easy to separate cresol in the aqueous layer, so that excessive cresol is included in the aqueous layer to cause an environmental problem, and hydroxide inorganic ions are included in cresol to lower cresol purity.

In addition, when the organic solvent is included at more than 200 parts by weight with respect to the reaction production mixture including cresol, the content of the organic solvent in cresol is high after the extraction process, so that a separate process for separating the organic solvent is needed, and thus, economic feasibility is deteriorated.

In addition, according to another exemplary embodiment of the present invention, it is preferred that the step of extracting with an organic solvent is repeated about 2 to 5 times.

Cresol is a toxic compound, which may be absorbed through the skin, the mucous membrane, or the like even in a small amount, and concentrated and distributed in the blood or organs such as liver, brain, lungs, and kidneys to show toxicity to the human body, and thus, in terms of environment and safety, it is important to more clearly remove cresol remaining in the aqueous layer.

As an exemplary embodiment of the present invention, when the step of extracting with an organic solvent is repeated twice or more or about 2 to 5 times, cresol present in the aqueous layer may be decreased to about 500 ppm or less, more preferably about 100 ppm or less, and more preferably about 10 ppm or less which is a limit to be detected with liquid chromatography, and thus, it may be very advantageous in terms of environment.

The following step is separating extracted cresol in an organic layer and DTE and recirculating the separated DTE to the reaction step to move equilibrium toward cresol so that DTE production is suppressed. When the amount of recirculated cresol is increased so that the amount of recirculated DTE reaches 7 to 8 mol % of produced cresol, the DTE by-product is not produced from the reacted product anymore and only cresol is produced, and thus, there may be a great economic effect in terms of DTE production as a side reaction, costs of disposing the DTE, and the like. Separation of cresol and DTE may be performed by distillation, and as a specific example, a distillation tower for separation may have a total of 100 stages and the distillation may be performed with a dividing wall column (DWC) having a top temperature of 140.7° C., a top pressure of 0.1 barg, a bottom temperature of 206.6° C., and a bottom pressure of 0.14 barg, but is not limited thereto.

Hereinafter, actions and effects of the present invention will be described in more detail, with reference to the specific examples of the present invention. However, the examples are illustrative only, and not intended to limit the scope of the present invention.

Example 1

To a continuous reactor, NaOH (10 wt %) chlorotoluene: DTE at a mole ratio of 2.5:1:0.08 were fed, conditions of 400° C. and 300 atm were maintained for 30 minutes, and the reaction was carried out under a basic condition.

After the reaction, 28 g of hydrochloric acid was added to 100 g of the resulting product to adjust pH to 1.

As shown in the following Table 1, an organic solvent was added, stirring was performed for 30 minutes to evenly mix them, cresol as the product was separated from an aqueous layer, and after the phase separation, the content of cresol in the aqueous layer was analyzed using liquid chromatography. As a result, cresol and DTE produced were 92 mol %:8 mol %, and it was found that DTE as a side reaction product was no longer produced beyond the feed amount.

Comparative Example 1

The process was performed in the same manner as in Example 1 except that to a continuous reactor, NaOH (10 wt %) and chlorotoluene were fed at a mole ratio of 2.5:1, conditions of 400° C. and 300 atm were maintained for 30 minutes, and the reaction was carried out under a basic condition. As a result of measuring the contents of cresol and DTE in the aqueous layer produced, it was found that DTE was produced at a mole ratio of 92.3:7.7.

Example 2

The process was performed in the same manner as in Example 1 except that recovered DTE was fed at 4 mol % to chlorotoluene. As a result, it was found that the content of DTE as a by-product was produced at 7.8 mol %, and thus, 3.7 mol % of DTE was more produced than the feed amount.

From the examples and the comparative example, it was found that by feeding recirculated DTE to a reaction step, DTE was not produced anymore, and thus, unnecessary DTE production was suppressed, thereby providing a new method of preparing cresol which is economical and environmentally excellent.

The invention claimed is:

1. A method of preparing cresol by a process of reacting halotoluene and a basic aqueous solution, the method comprising:

separating DTE which is a by-product of the process and refeeding the DTE into the reaction process of halotoluene and a basic aqueous solution.

2. The method of preparing cresol of claim 1, wherein the method includes:

reacting the halotoluene and the basic aqueous solution in a reactor;

adding an acid for acidification;

adding an organic solvent to extract cresol from an aqueous layer; and separating the by-product from the extracted cresol in the aqueous layer and refeeding the by-product into the reactor of the reaction process to perform the reaction.

3. The method of preparing cresol of claim 2, wherein the acidification is adding the acid for acidification to a range of pH −5 to 2.5.

4. The method of preparing cresol of claim 1, wherein the reacting of halotoluene and a basic aqueous solution is carried out in a condition of pH 11 or more.

5. The method of preparing cresol of claim 1, wherein the reacting of halotoluene and a basic aqueous solution is carried out at a temperature of 100 to 450° C. under a pressure of 100 to 500 atm.

6. The method of preparing cresol of claim 2, wherein the acidification is carried out using the acid having a pKa value of −2 or less.

7. The method of preparing cresol of claim 1, wherein the organic solvent is used at 10 to 200 parts by weight with respect to 100 parts by weight of a reaction production mixture including the cresol.

8. The method of preparing cresol of claim 2, wherein the extracting with an organic solvent is repeated twice or more.

* * * * *